United States Patent
Abels et al.

(10) Patent No.: US 7,134,872 B2
(45) Date of Patent: *Nov. 14, 2006

(54) COLORED ORTHODONTIC BRACKETS

(76) Inventors: Norbert Abels, Allaestrasse 30a, 66424 Homburg (DE); Claus-H. Backes, St. Wendeler Strasse 45, 66113 Saabrücken (DE)

( * ) Notice: Subject to any disclaimer, the term of this patent is extended or adjusted under 35 U.S.C. 154(b) by 155 days.

This patent is subject to a terminal disclaimer.

(21) Appl. No.: 10/932,634

(22) Filed: Sep. 2, 2004

(65) Prior Publication Data

US 2006/0046223 A1    Mar. 2, 2006

(51) Int. Cl.
*A61C 7/00*    (2006.01)

(52) U.S. Cl. .......................................................... 433/8

(58) Field of Classification Search .................... 433/8, 433/10

See application file for complete search history.

(56) References Cited

U.S. PATENT DOCUMENTS

| | | | | |
|---|---|---|---|---|
| 5,096,417 A | * | 3/1992 | Greenberg et al. | 433/24 |
| 5,116,885 A | * | 5/1992 | Hattori et al. | 523/200 |
| 5,607,299 A | | 3/1997 | Nicholson | 433/3 |
| 5,716,208 A | * | 2/1998 | Forman | 433/8 |
| 5,857,849 A | * | 1/1999 | Kurz | 433/10 |
| 6,142,775 A | | 11/2000 | Hansen et al. | 433/8 |
| 6,350,792 B1 | * | 2/2002 | Smetana et al. | 522/81 |
| 6,506,049 B1 | * | 1/2003 | Hanson | 433/11 |
| 6,663,385 B1 | * | 12/2003 | Tepper | 433/11 |
| 2002/0119414 A1 | * | 8/2002 | Orikasa | 433/10 |

FOREIGN PATENT DOCUMENTS

| | | |
|---|---|---|
| DE | 20314121 U1 | 1/2004 |
| WO | WO 2004/004592 | 1/2004 |

* cited by examiner

*Primary Examiner*—Cary E. O'Connor
(74) *Attorney, Agent, or Firm*—Workman Nydegger (57) ABSTRACT

An orthodontic bracket that includes coloring means for coloring to create a desired aesthetic appearance. The orthodontic bracket includes a bracket base, an arch wire slot formed in the bracket base, and a ligation cover hingedly connected to the bracket base and selectively rotatable relative to the bracket base between an open, non-ligating position relative to the arch wire slot and a closed, ligating position relative to the arch wire slot. According to one embodiment, the coloring means a colored dye or pigment impregnating the thermoplastic resin from which the bracket base and/or ligation cover are formed. According to another embodiment, the coloring means for coloring comprises a curable resin containing a colored dye or pigment that has been applied and cured over at least a portion of the bracket base and/or ligation cover.

17 Claims, 8 Drawing Sheets

COLORED ORTHODONTIC BRACKETS

BACKGROUND OF THE INVENTION

1. The Field of the Invention

The present invention relates to orthodontic brackets, more particularly to self-ligating orthodontic brackets that include a base, at least one slot for receiving an arch wire, and a ligating cover.

2. The Relevant Technology

Orthodontics is a specialized field of dentistry that involves the application of mechanical forces to urge poorly positioned, or crooked, teeth into correct alignment and orientation. Orthodontic procedures can be used for cosmetic enhancement of teeth, as well as medically necessary movement of teeth to correct underbites or overbites. For example, orthodontic treatment can improve the patient's occlusion, or enhanced spatial matching of corresponding teeth.

The most common form of orthodontic treatment involves the use of orthodontic brackets and wires, which together are commonly referred to as "braces." Orthodontic brackets, more particularly the orthodontic bases, are small slotted bodies configured for direct attachment to the patient's teeth or, alternatively, for attachment to bands which are, in turn, cemented or otherwise secured around the teeth. Once the brackets are affixed to the patient's teeth, such as by means of glue or cement, a curved arch wire is inserted into the slot of each bracket. The arch wire acts as a template or track to guide movement of the teeth into proper alignment. End sections of the arch wire are typically captured within tiny appliances known as "buccal tubes" affixed to the patient's molars.

There are two distinct classes of orthodontic brackets: those that require the use of ligatures to fasten the arch wire to the bracket, and those that are self-ligating. In brackets of the first class, small ligature wires are typically used to hold the arch wire in a securely seated position in the brackets. Ligatures or some other form of fastening means are essential to ensure that the tensioned arch wire is properly positioned around the dental arch, and to prevent the wire from being dislodged from the bracket slots during chewing of food, brushing of teeth, or application of other forces. One type of commercially available ligature is a small, elastomeric O-ring, which is installed by stretching the O-ring around small wings known as "tie wings" that are connected to the bracket body. Metal ligatures are also used to retain arch wires within the bracket slots.

In an effort to simplify the process of installing braces, a variety of self-ligating brackets have been developed. The term "self-ligating bracket" refers to a class of orthodontic brackets that include some sort of cover, whether separate from or hingedly or slidably attached to the base, which encloses or otherwise retains the arch wire within the slot of the base.

Besides the difficulties associated with the general discomfort of orthodontic brackets, many patients dislike the appearance of installed orthodontic brackets. Most existing orthodontic brackets are formed of metal, and result in a rather particular aesthetic appearance, which some patients dislike. It would be an improvement in the art to provide a self-ligating orthodontic bracket that allows the patient some flexibility in creating a desired aesthetic look, while still providing ease of use, inexpensive manufacturing, strength, and durability.

BRIEF SUMMARY OF THE PREFFERED EMBODIMENTS

The present invention is directed to an orthodontic bracket that includes coloring means for coloring the bracket to create a desired aesthetic appearance. The orthodontic bracket includes a bracket base, an arch wire slot formed in the bracket base, a ligation cover hingedly connected to the bracket base and selectively rotatable relative to the bracket base between an open, non-ligating position relative to the arch wire slot and a closed, ligating position relative to the arch wire slot, and coloring means for coloring at least a portion of the bracket base and/or the ligation cover. According to one embodiment, the coloring means for coloring comprises a colored dye or pigment impregnating the thermoplastic resin from which the bracket base and/or ligation cover are formed. According to another embodiment, the coloring means for coloring comprises a curable resin containing a colored dye or pigment that has been applied and cured over at least a portion of the bracket base and/or ligation cover.

The orthodontic bracket may be formed by injection molding the thermoplastic resin material from which it is formed. In addition, the bracket base and ligation cover may be integrally formed together as a single piece. Examples of suitable thermoplastic resins include, but are not limited to, polyamides (e.g., nylon), acetal polymers, polyetherimides, polycarbonates, polyarylether ketones, polysulfones, and polyphenylsulfones.

Any colored dye or pigment that is compatible with the bracket material may be used as coloring means for coloring, whether the colored dye or pigment is impregnated into the bracket forming resin material or included in a curable resin that is applied to the bracket base and/or cover and subsequently light or chemical cured. According to one embodiment, the colored dye or pigment may comprise food coloring.

In embodiments where a curable resin containing a colored dye or pigment is applied over at least a portion of the bracket base and/or ligation cover, the curable resin may be applied during manufacture of the orthodontic bracket or clinically by the orthodontist. Although other manufacturing stage application methods may be used, according to one embodiment, the curable resin is applied during manufacturing by spin coating, as known in the art. Although other clinical application methods may be used, according to another embodiment, the curable resin is applied clinically by brush coating.

One embodiment of the orthodontic bracket includes an elongate film hinge and a hinge guide structure. The elongate film hinge is attached at one end to the bracket base and at an opposite end to the ligation cover so as to hingedly connect the ligation cover to the bracket base. The hinge guide structure may be disposed on the ligation cover or bracket base, and provides a curved surface around which the elongate film hinge bends when the ligation cover is rotated relative to the bracket base. The curved surface causes the elongate film hinge to bend over a significant portion of its entire length.

Including an elongate film hinge and hinge guide structure is advantageous as it results in an especially strong and durable orthodontic bracket. The combination of the elongate film hinge and the hinge guide structure allows the forces associated with opening and closing the bracket to be distributed along a significant length of the elongate film hinge, rather than concentrating the forces at a point or line where bending occurs.

According to one embodiment, the curved surface of the hinge guide structure forms a part of a cam structure that is attached to an inner surface of the ligation cover and that extends toward the bracket base. The cam structure also preferably includes a camming surface, distal to the film hinge, which interacts with the bracket base so as to bias the ligation cover toward the open, non-ligating position. This makes it easier for the dental practitioner to insert the arch wire into the arch wire slot.

The orthodontic bracket preferably includes a latch mechanism that selectively locks and unlocks the ligation cover in the closed, ligating position. The latch mechanism may comprise an angled keyway and a locking tongue. The angled keyway may be formed within a side of the bracket base distal to the elongate film hinge. The locking tongue extends from an end of the cover distal to the elongate film hinge. The locking tongue is configured to selectively fit within the angled keyway and lock the ligation cover to the bracket base in the closed, ligating position.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

A detailed description of the invention will now be provided with specific reference to Figures illustrating preferred embodiments of the invention. It will be appreciated that like structures will be provided with like reference designations.

II. Exemplary Orthodontic Brackets

Figure 1A:
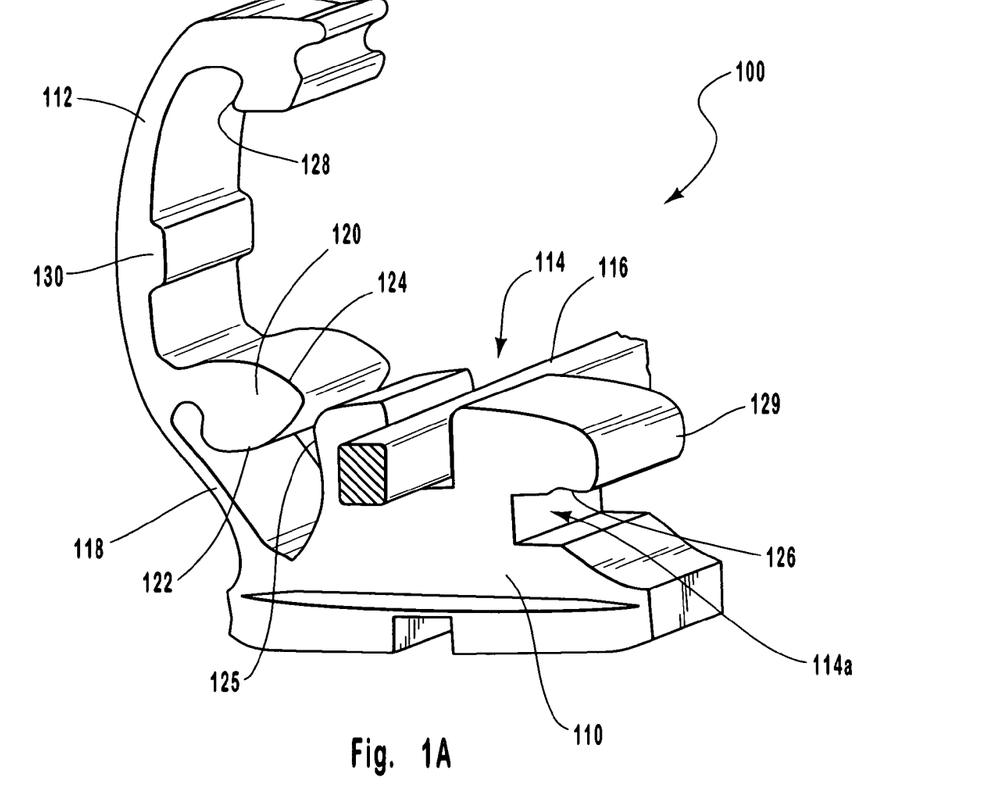
FIGS. 1A–1B illustrate an exemplary self-ligating orthodontic bracket according to the present invention.
Figure 1B:
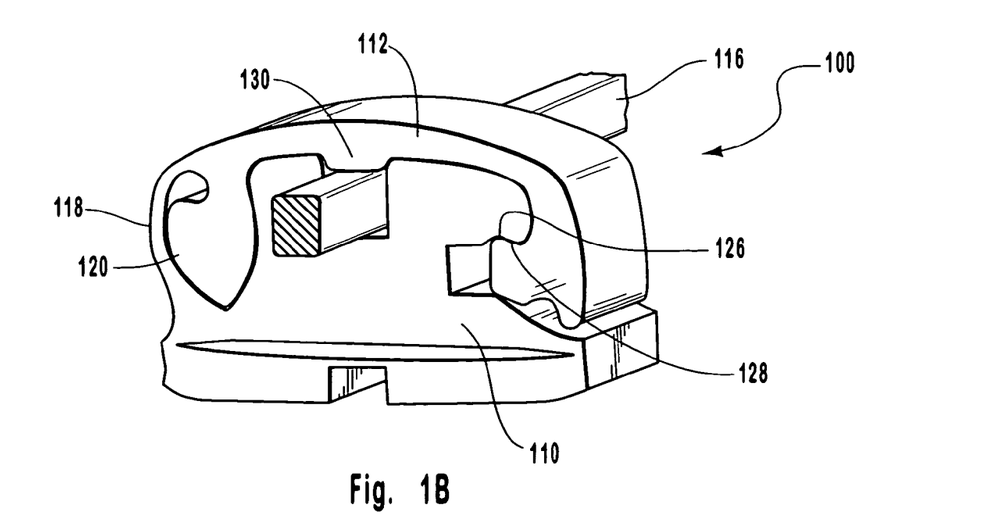

The orthodontic bracket shown in FIGS. 1A–1B may be manufactured in one single piece as an injection molded plastic part. The orthodontic bracket 100 has a base 110 to which a cover 112 is hingedly attached. A slot 114 open to the upper side of the base 110 is provided near the center of said base 110 and serves for the insertion of an arch wire 116 therein. An additional arch wire slot 114a may also be provided. The arch wire 116, shown with a square cross-section (any other cross section known in the art could be used), is arranged inside the slot 114 and serves to correct tooth alignment in a known manner.

The cover 112 is hingedly connected to the bracket base 110 by a single elongate film hinge 118. The cover 112 is such that it may be selectively rotated between an open and a closed position relative to the arch wire slot 114. The cover 112 maintains the arch wire 116 within the slot 114 when the cover is in the closed ligating position.

The elongate film hinge 118 of this embodiment is designed to bend along substantially its entire length rather than at a single point or line. This helps the hinge resist fatigue or fracture better than film hinges that bend along a single line.

The bracket embodiment illustrated in FIGS. 1A and 1B preferably includes an interactive cam structure 120 with a first curved surface 122 and a second curved surface 124. The first curved surface 122 interacts with the elongate film hinge 118 to provide a curved surface that helps ensure that the elongate film hinge 118 bends gradually over its entire length rather than abruptly at any specific locale. The second curved surface 122 is curved in such a way so that it interacts with a corresponding wall 125 of the base 110 so as to bias the ligation cover 112 in an open position relative to the bracket base 110 when the ligation cover 112 is in the open position. This improves access to arch wire slot 114, making insertion or removal of the arch wire 116 easier. The second curved surface 124 may, depending on the shape of the corresponding wall 125 of the bracket base 110, also act to bias the ligation cover 112 to remain in a closed position when in the closed position relative to the bracket base 110.

An angled keyway 126 is provided near one end of the base 110. The cover 112 contains a corresponding locking tongue 128 that enables the ligation cover 112 to be selectively locked or unlocked relative to the bracket base 110. The ligation cover 112 is locked to bracket base 110 (as seen in FIG. 1B) by closing the cover 112 so that the locking tongue 128 is inserted into angled keyway 126.

In the event that the arch wire 116 pushes against the cover 112 with sufficient force to cause the cover to bulge upwardly relative to the bracket base 110, rather than causing the tongue 128 to withdraw from the angled keyway 126, which could result in undesired disengagement of the cover 112, the locking tongue 128 is instead pulled more deeply into the angled keyway 126, thereby tightening the locking mechanism. This provides added safety. To open the cover, the locking tongue 128 is pulled out of angled keyway 126 and over an outer protrusion 129 of the bracket base 110.

Furthermore, a bearing protrusion 130 is provided at the inside and middle of the cover 112 to assist in fixing the arch wire 116 in the slot 114 while the cover 112 is in the closed state (FIG. 1B). The bearing protrusion 130 reduces the play in the system by effectively widening the ligation cover 112 in the vicinity of the arch wire slot 114.

Figure 1C:
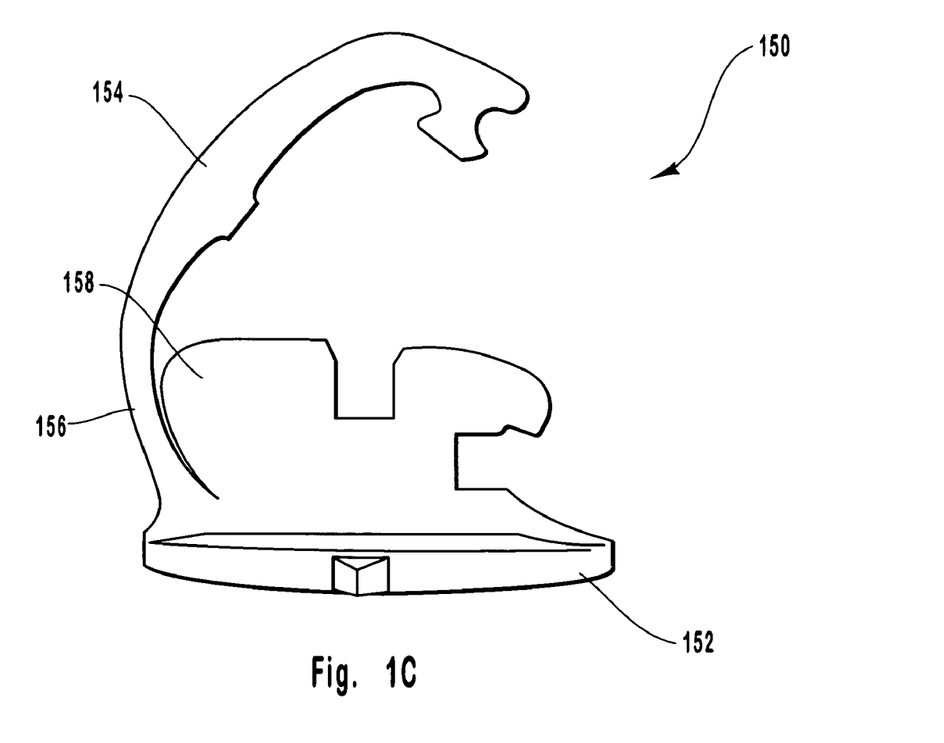
FIGS. 1C–1D illustrate an alternative self-ligating orthodontic bracket according to the invention.
Figure 1D:
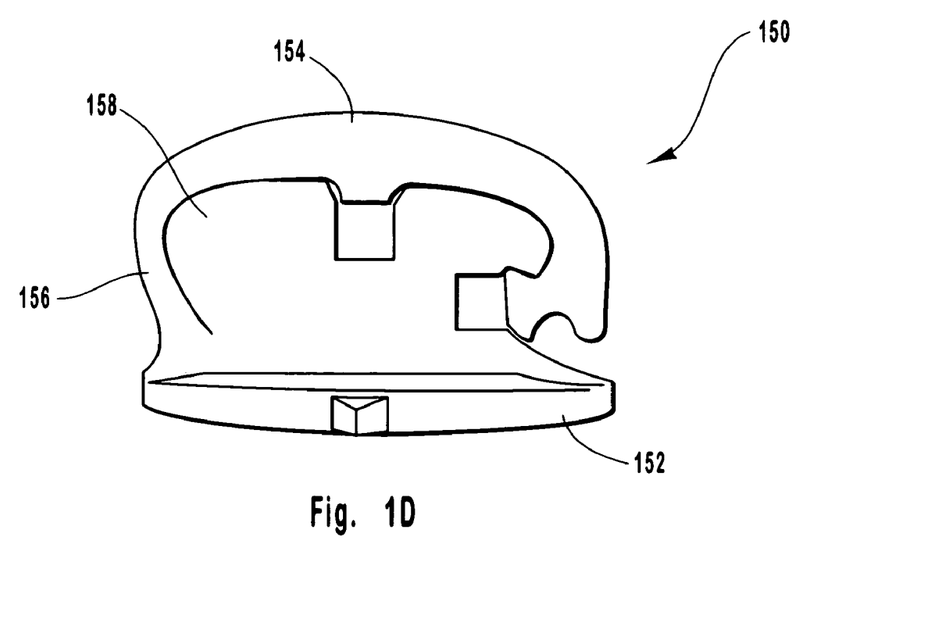

FIGS. 1C and 1D depict an alternative embodiment of an orthodontic bracket 150 that may include coloring means for coloring at least a portion of the bracket base 152 and/or ligation cover 154. Orthodontic bracket 150 does not include a cam structure. Instead, the orthodontic bracket 150 depicted in FIGS. 1C and 1D includes a bracket base 152 and a ligation cover 154 attached to the bracket base 152 by means of an elongate film hinge 156. The bracket base 152 further includes a curved end 158 that acts as a hinge guide in order to cause the elongate film hinge 156 to bend gradually over a significant portion of its entire length. In this way, the curved end 158 of the bracket base 152 acts in similar manner to the curved hinge-guiding surface 122 of the cam structure 120 of the orthodontic bracket 100 depicted in FIGS. 1A–1B. Thus, as the ligation cover 154 is moved from an open, non-ligating position (FIG. 1C) to a closed, ligating position (FIG. 1D), the elongate film hinge 156 at least partially abuts the curved end 158. The abutment between the elongate film hinge 156 and the curved end 158 causes the elongate film hinge 156 to bend gradually around the curved end 158 so as to better distribute the bending forces and bending angles along substantially the entire length of the elongate film hinge 156.

Figure 2A:
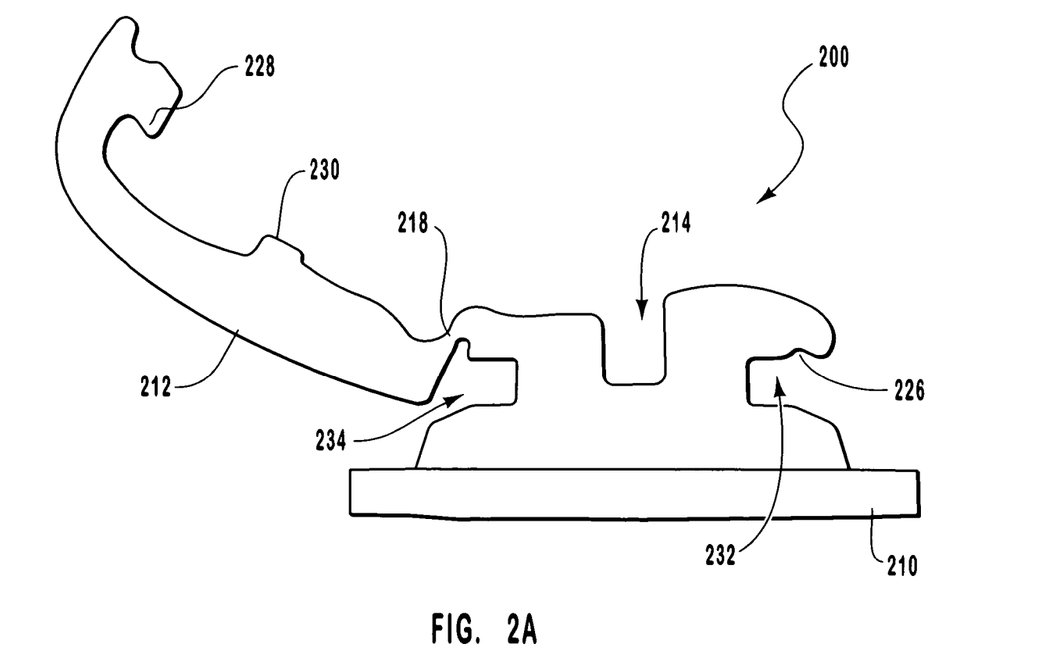
FIGS. 2A–2B illustrate another alternative self-ligating orthodontic bracket according to the invention.
Figure 2B:
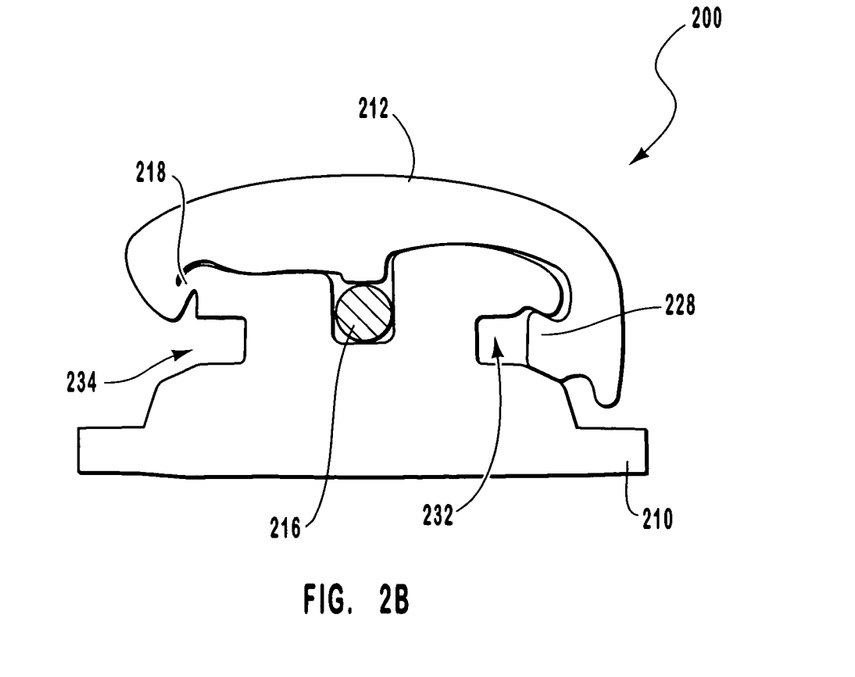

FIGS. 2A and 2B illustrate another alternative bracket embodiment that may include coloring means for coloring at least a portion of the bracket base 210 and/or ligation cover 212. Bracket 200 is similar to the bracket illustrated in FIGS. 1A–1B in that it includes a bracket base 210, a ligation cover 212, a slot 214, an arch wire 216 (seen in FIG. 2B), an angled keyway 226, a locking tongue 228, and a bearing protrusion 230. This example differs from the bracket illustrated in FIGS. 1A–1B in that although it also uses a film hinge 218 to attach the ligation cover 212 to the bracket base 210, the hinge 218 is not as elongated as hinge 118 shown in FIGS. 1A–1B. Bracket 200 may further include additional arch wire slots 232 and 234 for use with additional or alternative arch wires as known in the art.

Figure 3A:
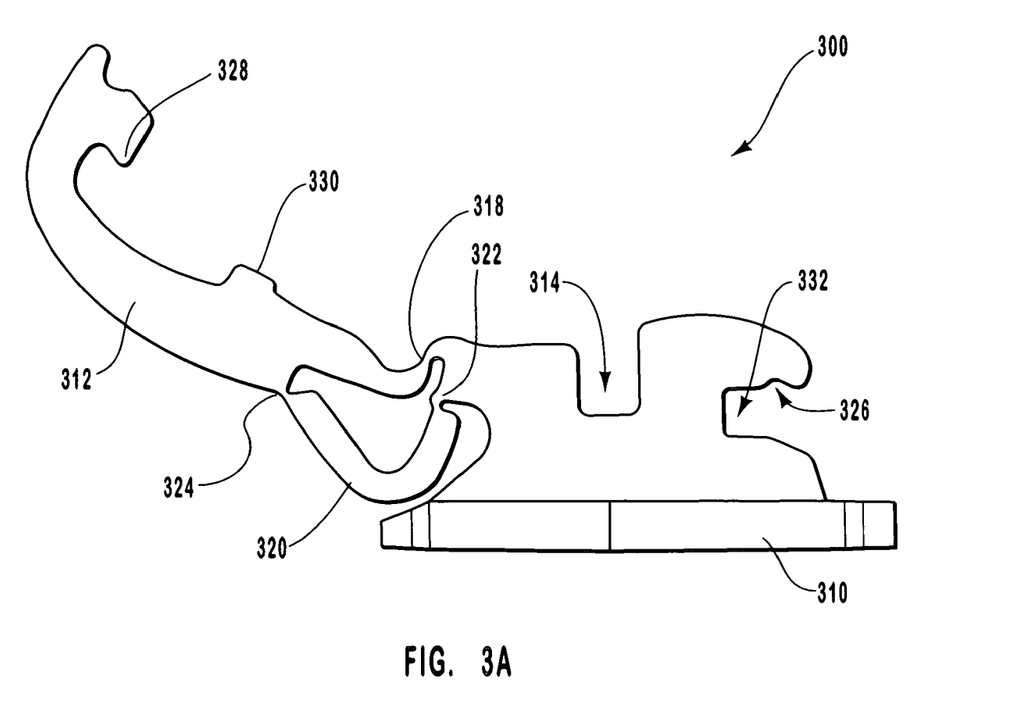
FIGS. 3A–3B illustrate another alternative self-ligating orthodontic bracket according to the invention.
Figure 3B:
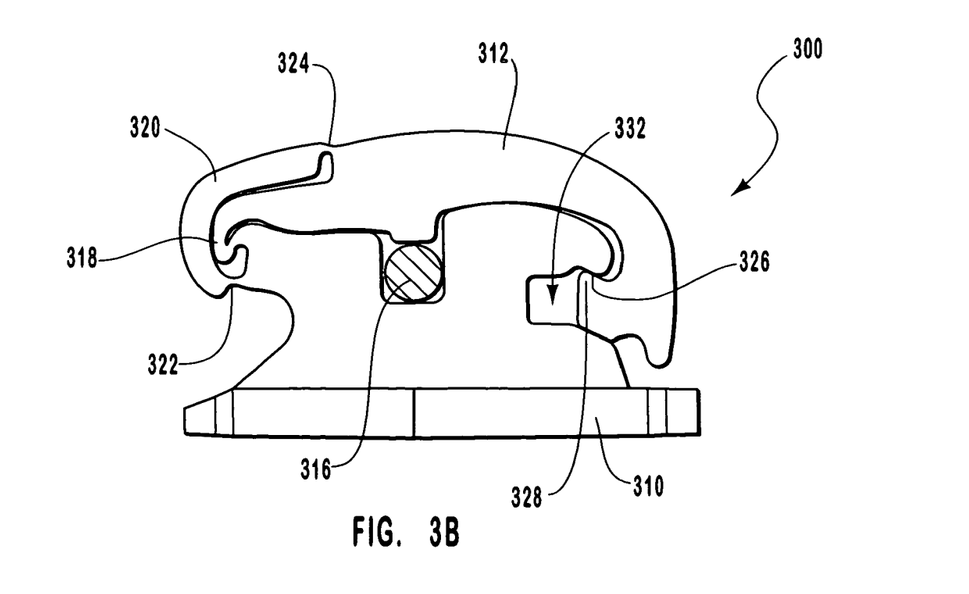

FIGS. 3A and 3B illustrate another alternative bracket embodiment that may include coloring means for coloring at least a portion of the bracket base 310 and/or ligation cover 312. Bracket 300 includes a bracket base 310, a ligation cover 312, a slot 314, an arch wire 316 (seen in FIG. 3B), a main film hinge 318, an angled keyway 326, a locking tongue 328, a bearing protrusion 330, and an additional arch wire slot 332. This example differs from that illustrated in FIGS. 2A–2B in that it further has a spring element 320 attached at one end of the bracket base 310 by a film hinge 322 and at an opposite end to the ligation cover 312 by a film hinge 324.

Figure 4A:
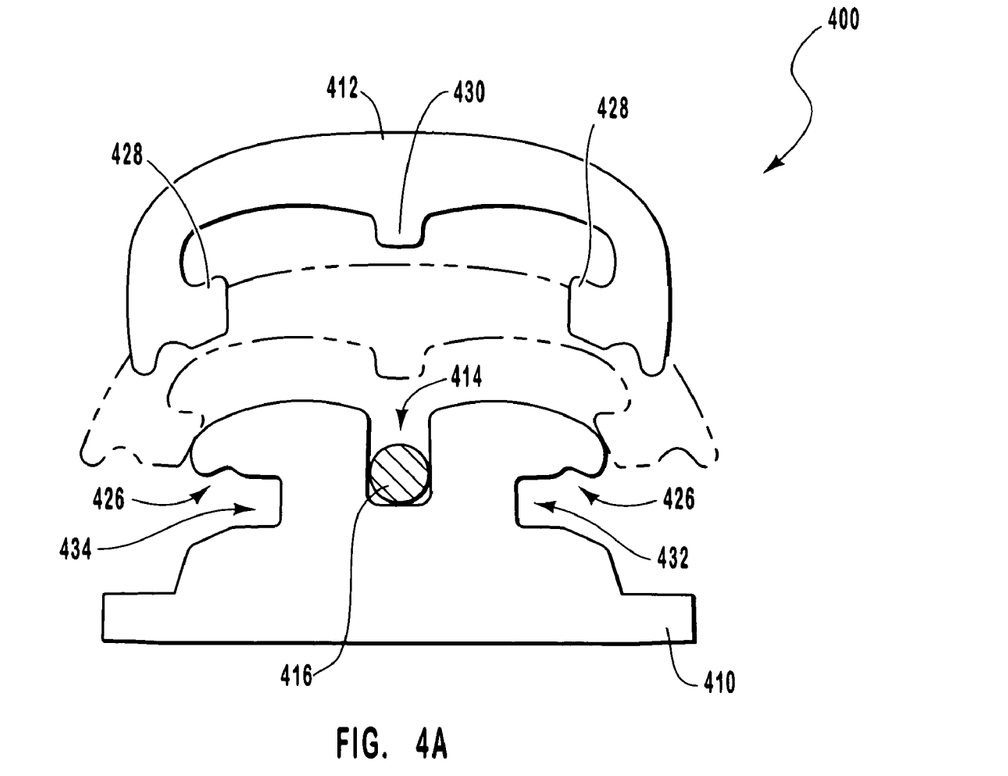
FIGS. 4A–4B illustrate yet another alternative self-ligating orthodontic bracket according to the invention.
Figure 4B:
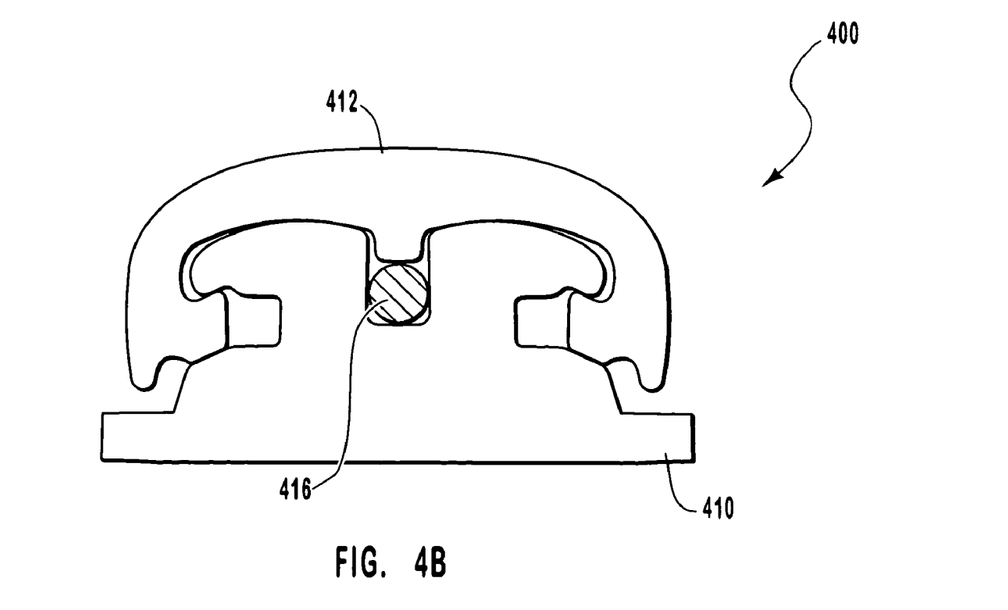

FIGS. 4A and 4B illustrate yet another alternative bracket embodiment that may include coloring means for coloring at least a portion of the bracket base 410 and/or ligation cover 412. Bracket 400 includes a bracket base 410, a ligation cover 412, a slot 414, an arch wire 416, a pair of angled keyways 426, a pair of locking tongues 428, a bearing protrusion 430, and additional arch wire slots 432 and 434. This example differs from those illustrated in FIGS. 1–3 in that it includes no hinge between the base 410 and the cover 412. The bracket base 410 could be used without the cover 412 as a traditional bracket requiring ligatures. Using the cover 412 results in a self-ligating bracket with a uniform, closed, smooth surface across the top surface of the bracket 400, which is beneficial for patient comfort and hygiene.

Various other bracket designs are disclosed in U.S. application Ser. No. 09/784,525, filed Feb. 15, 2001; U.S. application Ser. No. 09/914,737, filed Aug. 29, 2001; and U.S. application Ser. No. 09/953,400, filed Sep. 12, 2001. For purposes of disclosing exemplary orthodontic bracket designs, the foregoing U.S. patent applications are incorporated by reference.

The orthodontic brackets may be formed by injection molding the thermoplastic resin material that it is formed from, either as separate pieces or as a single piece. Examples of suitable thermoplastic resins include, but are not limited to, polyamides, acetal polymers, polyetherimides, polycarbonates, polyarylether ketones (e.g., PEEK), polysulfones, and polyphenylsulfones III. Exemplary Coloring Means According to one embodiment, the coloring means for coloring may comprise a colored dye or pigment impregnating the thermoplastic resin from which the bracket base and/or ligation cover are formed. According to an alternative embodiment, the coloring means for coloring may comprise a curable resin containing a colored dye or pigment that has been applied and cured over at least a portion of the bracket base and/or ligation cover. An advantage of the latter coloring means is that it allows for changes in the color of the brackets from an initial color.

Any colored dye or pigment that is compatible with the bracket material may be used as coloring means for coloring, whether the colored dye or pigment is impregnated into the bracket forming resin material or included in a curable resin that is applied to the bracket base and/or cover and subsequently light or chemical cured. According to one embodiment, the colored dye or pigment may comprise any of the various food colorings known in the art.

In embodiments where a curable resin containing a colored dye or pigment is applied over at least a portion of the bracket base and/or ligation cover, the curable resin may be applied during manufacture of the orthodontic bracket or clinically, by the orthodontist. Although other manufacturing stage application methods may be used, according to one embodiment, the curable resin is applied during manufacturing by spin coating, as will be known to those skilled in the art.

Figure 5A:
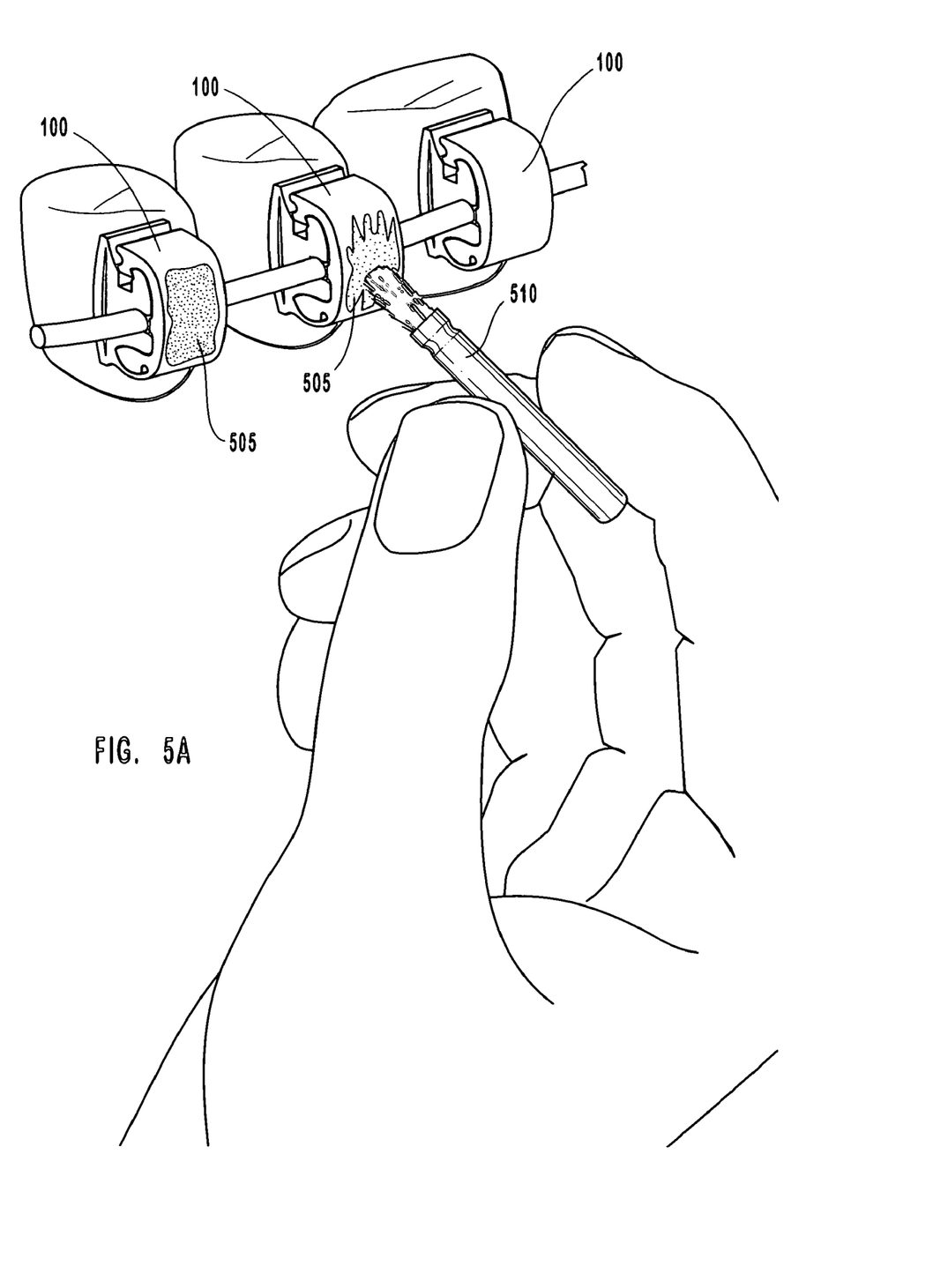
FIG. 5A illustrates application of a curable resin containing a colored dye or pigment over at least a portion of the ligation covers of several orthodontic brackets by brushing.
Figure 5B:
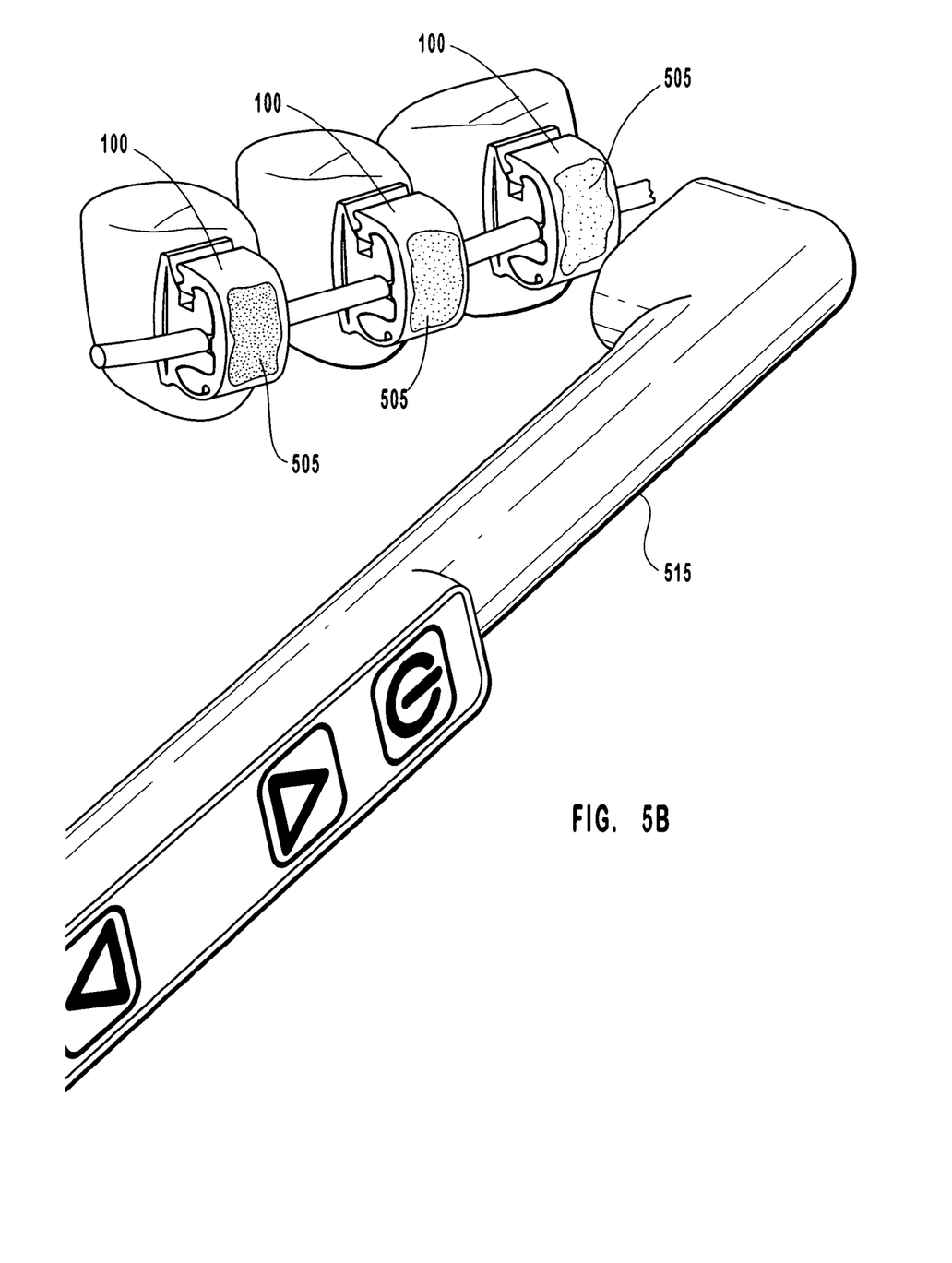
FIG. 5B illustrates light curing of the curable resin applied in FIG. 5A.
Figure 6:
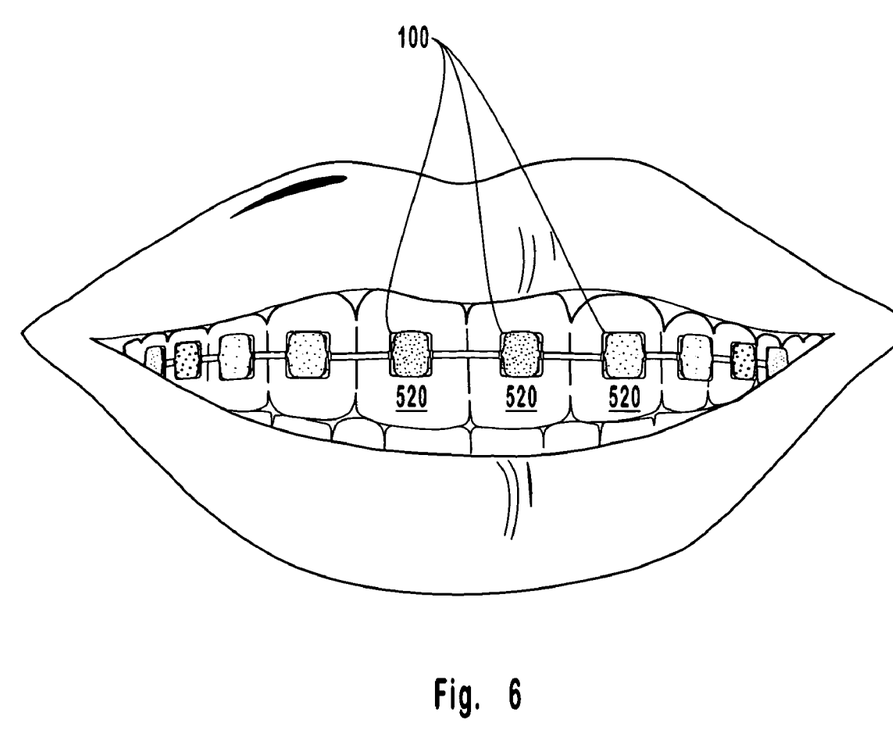
FIG. 6 illustrates bonded orthodontic brackets having a light cured colored coating.

Although other clinical application methods may be used, according to one embodiment, the curable resin is applied clinically by brush coating, as illustrated in FIG. 5A. A brush 510 or other applicator is used to apply a curable resin 505 that includes a colored dye or pigment. Although any curable resin may be used, Ormocere, made by Fraunhofer in Wurzburg, Germany, is an example of a suitable curable resin that can be combined with a colored dye or pigment (e.g., food coloring) and then light cured with a light emitting device 515 as illustrated in FIG. 5B. According to an alternative embodiment, a chemically curable resin may be used. FIG. 6 illustrates the orthodontic brackets 100 as bonded to the teeth 520 of a patient. According to a further embodiment, small decorations (e.g., decorative jewelry, pictures, or designs) may be bonded to the orthodontic brackets, as desired.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An orthodontic bracket formed from a thermoplastic resin, comprising:
   a bracket base;
   at least one arch wire slot formed in the bracket base adapted to receive an arch wire therein;
   a ligation cover joined to the bracket base by a single elongate film hinge so that the ligation cover can be selectively moved relative to the bracket base between an open, non-ligating position relative to the arch wire slot and a closed, ligating position relative to the arch wire slot, and wherein the elongate film hinge is bendable along substantially its entire length rather than at a single point or line; and coloring means for coloring at least a portion of said bracket base or said ligation cover.

2. An orthodontic bracket as recited in claim 1, wherein the coloring means for coloring comprises a colored dye or pigment impregnating the thermoplastic resin from which the bracket base and/or ligation cover are formed.

3. An orthodontic bracket as recited in claim 2, wherein the colored dye or pigment comprises at least one food colorant.

4. An orthodontic bracket as recited in claim 1, wherein the orthodontic bracket is formed by injection molding the thermoplastic resin.

5. An orthodontic bracket as recited in claim 1, wherein the thermoplastic resin comprises at least one of a polyamide, an acetal polymer, a polyetherimide, a polycarbonate, a polyarylether ketone, a polysulfone, and a polyphenylsulfone.

6. An orthodontic bracket as recited in claim 1, wherein the coloring means for coloring comprises a curable resin containing a colored dye or pigment that has been applied and cured over at least a portion of the bracket base or ligation cover.

7. An orthodontic bracket as recited in claim 6, wherein the colored dye or pigment comprises at least one food colorant.

8. An orthodontic bracket as recited in claim 1, further comprising a hinge guide structure disposed on the ligation cover or bracket base, the hinge guide structure providing a curved surface around which the elongate film hinge bends when the ligation cover is selectively rotated relative to the bracket base so that the elongate film hinge bends over a significant portion of its entire length.

9. An orthodontic bracket as recited in claim 8, wherein the curved surface interacts with the elongate film hinge so as to distribute bending forces along the significant portion of the entire length of the elongate film hinge when the ligation cover is selectively rotated relative to the bracket base.

10. An orthodontic bracket as recited in claim 9, wherein the hinge guide structure comprises a curved surface, proximal to the film hinge, of a cam structure that is attached to an inner surface of the ligation cover and that extends toward the bracket base. wherein the cam structure comprises a camming surface, distal to the film hinge, that interacts with the bracket base so as to bias the ligation cover toward the open, non-ligating position.

11. An orthodontic bracket as recited in claim 8, wherein the elongate film hinge has a cross-sectional thickness that is less than the cross-sectional thicknesses of the ligation cover and bracket base where the ligation cover and bracket base are attached to the elongate film hinge.

12. An orthodontic bracket as recited in claim 8, wherein the elongate film hinge interacts with the ligation cover in a manner so that the ligation cover is not biased toward the closed, ligating position.

13. An orthodontic bracket as recited in claim 1, further comprising a latch mechanism that selectively locks and unlocks the ligation cover in the closed, ligating position.

14. An orthodontic bracket formed from a thermoplastic resin, comprising:
a bracket base;
at least one arch wire slot formed in the bracket base adapted to receive an arch wire therein; and
a ligation cover joined to the bracket base by a single elongate film hinge so that the ligation cover can be selectively moved relative to the bracket base between an open, non-ligating position relative to the arch wire slot and a closed, ligating position relative to the arch wire slot, and wherein the elongate film hinge is bendable along substantially its entire length rather than at a single point or line; and
wherein at least the bracket base or ligation cover are formed from a thermoplastic resin impregnated with a colored dye or pigment.

15. An orthodontic bracket as recited in claim 14, wherein orthodontic bracket is formed by injection molding a thermoplastic resin, wherein the bracket base and ligation cover are integrally formed together as a single piece.

16. An orthodontic bracket formed from a thermoplastic resin, comprising:
a bracket base;
at least one arch wire slot formed in the bracket base adapted to receive an arch wire therein;
a ligation cover joined to the bracket base by a single elongate film hinge so that the ligation cover can be selectively moved relative to the bracket base between an open, non-ligating position relative to the arch wire slot and a closed, ligating position relative to the arch wire slot, and wherein the elongate film hinge is bendable along substantially its entire length rather than at a single point or line; and
a curable resin containing a colored dye or pigment applied and cured over at least a portion of the bracket base or ligation cover.

17. An orthodontic bracket as recited in claim 16, wherein the bracket base and ligation cover are formed by injection molding the thermoplastic resin, wherein the bracket base and ligation cover are integrally formed together as a single piece.

* * * * *